United States Patent [19]

Cesarman et al.

[11] Patent Number: 5,908,773
[45] Date of Patent: Jun. 1, 1999

[54] KSHV POSITIVE CELL LINES

[75] Inventors: Ethel Cesarman, Hoboken, N.J.;
Leandros Arvanitakis, New York, N.Y.; Daniel M. Knowles, Forest Hills, N.Y.; Enrique Mesri, Bronx, N.Y.

[73] Assignee: Cornell Research Foundation, Inc., Ithaca, N.Y.

[21] Appl. No.: 08/717,291

[22] Filed: Sep. 20, 1996

[51] Int. Cl.$^6$ ............................ C12N 7/00; A61K 39/245
[52] U.S. Cl. .................................... 435/235.1; 435/91.33; 435/372; 474/229.1
[58] Field of Search ................................... 435/135, 5, 6, 435/372, 41, 235.1, 91.33; 424/229.1

[56] References Cited

PUBLICATIONS

Chang, et al, 1994, Science, vol. 266, pp. 1865–1869.
Cesarman et al, 1995, Blood, vol. 86, pp. 2708–2714.
Boshoff et al, 1995, Nature Medicine, vol. 1, pp. 1274–1278.
Foreman et al, 1997, N.E.J.M., vol. 336, pp. 163–171.
Rennie et al, 1996, Nature Med., vol 2, pp. 342–346.
Nador, et al., "Herpes–Like DNA Sequences in a Body–Cavity–Based Lymphoma in the HIV–Negative Patient," *The New England Journal of Medicine*, 333(14):943 (1995) (abstract).
Walts, et al., "Diagnosis of Malignant Lymphoma in Effusions from Patients with AIDS by Gene Rearrangement," *A.J.C.P.*, 94(2):170–75 (1990).
Green, et al., "Primary Lymphomatous Effusions in AIDS: A Morphological, Immunophenotypic, and Molecular Study," *Modern Pathology*, 8(1):39–45 (1995).
Lin, et al., "Precision of Genotyping of Epstein–Barr Virus by Polymerase Chain Reaction Using Three Gene Loci (EBNA–2, EBNA–3C, and EBER): Predominance of Type A Virus Associated With Hodgkin's Disease," *Blood*, 81(12):3372–81 (1993).
Chadburn, et al., "CD30 (Ki–1) Positive Anaplastic Large Cell Lymphomas in Individuals Infected With the Human Immunodeficiency Virus," *Cancer*, 72(10):3078–90 (1993).
Knowles, et al., "Molecular Genetic Analysis of Three AIDS–Associated Neoplasms of Uncertain Lineage Demonstrates Their B–Cell Derivation and the Possible Pathogenic Role of the Epstein–Barr Virus," *Blood*, 73(3):792–99 (1989).
Biesinger, et al., "Stable Growth Transformation of Human T Lymphocytes by Herpesvirus saimiri," *Immunology*, 89:3116–19 (1992).
Mesri, et al., "Human Herpesvirus–8/Kaposi's Sarcoma–Associated Herpesvirus is a New Transmissible Virus That Infects B Cells," *J. Exp. Med.*, 183:2385–90 (1996).
Baer et al., "DNA Sequence and Expression of the B95–8 Epstein–Barr Virus Genome," *Nature*, 310:207–211 (1984).
Cameron et al., "The 160,000–M$_r$ Virion Protein Encoded at the right End of the Herpesvirus Saimiri Genome Is Homologous to the 140,000–M$_r$ Membrane Antigen Encoded at the Left End of the Epstein–Barr Virus Genome," *Journal of Virology*, 61:2063–2070 (1987).

Albrecht et al., "Primary Structure of the Herpesvirus Saimiri Genome," *Journal of Virology*, 66:5047–5058 (1992).
Nicholas et al., "Herpesvirus Saimiri Encodes Homologues of G Protein–Coupled Receptors and Cyclins," *Nature*, 355:362–365 (1992).
Ambroziak et al., "Herpes–Like Sequences in HIV–Infected and Uninfected Kaposi's Sarcoma Patients," *Science*, 268:582–583 (1995).
Boshoff et al., "Kaposi's–Sarcoma–Associated Herpesvirus In HIV–Negative Kaposi's Sarcoma," *The Lancet* 345:1043–1044 (1995).
Cesarman et al., "Kaposi's Sarcoma–Associated Herpesvirus–Like DNA Sequences in Aids–Related Body–Cavity–ased Lymphomas," *The New England Journal of Medicine*, 332:1186–1191 (1995).
Dupin et al., *New England Journal of Medicine*, p. 798 (1995).
Dupin et al., "Herpesvirus–Like DNA Sequences In Patients With Mediterranean Kaposi's Sarcoma," *The Lancet*, 345:761–762 (1995).
Karcher et al., "Herpes–Like DNA Sequences, Aids–Related Tumors, and Castleman's Disease," *The New England Journal of Medicine*, 333:797–798 (1995).
Moore et al., "Detection of Herpesvirus–Like DNA Sequences in Kaposi's Sarcoma in Patients With and Those Without HIV Infection," *The New England Journal of Medicine*, 332:181–191 (1995).
Noel, "Kaposi's Sarcoma and KSHV," *The Lancet*, 346:1359 (1995).
Schalling et al., "A Role For A New Herpes Virus (KSHV) In Different Forms of Kaposi's Sarcoma," *Nature Medicine*, 1:707–708 (1995).
Shingadia et al., "Kaposi's Sarcoma and KSHV," *The Lancet*, 346:1359–1360 (1995).
Soulier et al., "Kaposi's Sarcoma–Associates Herpesvirus–Like Sequences In Multicentric Castleman's Disease," *Blood*, 86:1276–1280 (1995).

(List continued on next page.)

*Primary Examiner*—Mary E. Mosher
*Assistant Examiner*—Ali R. Salimi
*Attorney, Agent, or Firm*—Nixon, Hargrave, Devans & Doyle LLP

[57] ABSTRACT

The invention provides a cell line comprising Kaposi's sarcoma-associated herpesvirus (KSHV). Preferably, the cell line is a body cavity-based lymphoma cell line, and more preferably, the cell line does not harbor Epstein-Barr virus. Two cell lines designated BC-2 and BC-3 are thus provided. These cell lines can be used in a method of propagating KSHV. The method comprises culturing the cell line, wherein the KSHV within the cell line thereby propagates. The BC-3 cell line, in particular, can be used in a method of propagating KSHV in the absence of Epstein-Barr virus. The method comprises culturing the cell line designated BC-3, wherein the KSHV within the cell line thereby propagates. Further provided is a purified viral suspension of KSHV, as well as a composition comprising purified KSHV and a suitable carrier.

4 Claims, No Drawings

OTHER PUBLICATIONS

Whitby et al., "Detection of Kaposi Sarcoma Associated Herpesvirus in Peripheral Blood of HIV–Infected Individuals and Progression to Kaposi's Sarcoma," *The Lancet*, 346:799–802 (1995).

Gessain et al., "Kaposi Sarcoma–Associated Herpes–Like Virus (Human Herpesvirus Type 8) DNA Sequences in Multicentric Castleman's Disease: Is There Any Relevant Association In Non–Human Immunodeficiency Virus–Infected Patients?," *Blood*, pp. 414–418 (1996).

Arvanitakis, et al., "Establishment and Characterization of a Body Cavity–Based Lymphoma Cell Line (BC–3) Harboring Kaposi's Sarcoma–Associated Herpesvirus (KSHV/HHV–8) in the Absence of Epstein–Barr Virus," *Blood* 88(7):001–007 (1996).

KSHV POSITIVE CELL LINES

The subject matter of this application was made with support from the United States Government under National Institutes of Health Grant Nos. AI 39192, CA 42710, EY 06337, and CA 68939.

FIELD OF INVENTION

The subject invention is directed to cell lines, and more particularly to cell lines comprising Kaposi's sarcoma-associated herpesvirus (KSHV) and to purified KSHV obtained from the cell lines.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Recent studies have shown the presence of DNA sequences belonging to a novel herpesvirus in Kaposi's sarcoma (KS) tissues (Chang et al. 1994). This virus has been called KS-associated herpesvirus (KSHV) and is provisionally designated human herpesvirus 8 (HHV-8). Although KSHV does not appear to be present in control tissues from non-acquired immunodeficiency syndrome (AIDS) patients (Chang et al. 1994; Moore and Chang 1995) or in the peripheral blood of normal blood donors (Whitby et al. 1995), it has been detected in two unique and distinctive categories of lymphoid proliferations, namely the primary effusion (body cavity-based) lymphomas (BCBL) (Cesarman et al. 1995a) and multicentric Castleman's disease (Soulier et al. 1995). The BCBLs are a distinct group of B-cell non-Hodgkin lymphomas presenting with a unique spectrum of clinical, morphologic, immunophenotypic, and molecular genetic characteristics that distinguish them from most AIDS-related lymphomas (Knowles et al. 1989; Walts et al. 1990; Green et al. 1995). More specifically, BCBLs tend to present in the pleural, pericardial, and/or abdominal cavities as lymphomatous effusions, usually in the absence of any identifiable tumor mass throughout the clinical course. They have an unusual immunophenotype in that they commonly express CD45 in the absence of other B- or T-cell lineage-restricted antigens. At the molecular level, they are characterized by a B-cell genotype as determined by clonal immunoglobulin (Ig) gene rearrangements, the presence of Epstein-Barr virus (EBV) and the lack of c-myc gene rearrangements (Cesarman et al. 1995a; Knowles et al. 1989; Green et al. 1995; Chadburn et al. 1993).

Sequence analysis of the KS330Bam and KS631Bam fragments of KSHV, as well as of cloned flanking regions (Chang et al. 1994), has shown homology to two viruses in particular: EBV (Baer et al. 1984) and herpesvirus saimiri (HVS) (Albrecht et al. 1992). Both of these viruses are members of the gammaherpesvirinae subfamily of herpesvirus, which members are characterized by their propensity to infect and transform lymphoblastoid cells (Roizman 1990; Liebowitz and Kieff 1993; Fleckenstein and Desrosiers 1982). The degree of homology, with amino acid identities in the range of 30% to 50%, is consistent with these sequences belonging to a novel member of the same family, which is referred to as Kaposi's sarcoma-associated herpesvirus (KSHV) (also referred to as human herpesvirus 8 or HHV-8). It is well known that EBV immortalizes B cells in vitro and is associated with certain malignant lymphomas, including Burkitt's lymphoma, some AIDS-related lymphomas, the post-transplantation lymphoproliferative disorders, and Hodgkin's disease (Liebowitz and Kieff 1993). HVS is a virus of squirrel monkeys (*Saimiri sciureus*) that can be isolated from peripheral blood mononuclear cells of healthy animals but causes fulminant T-cell lymphomas in New World primates other than its natural hosts (Fleckenstein and Desrosiers 1982). HVS is also capable of transforming human T lymphocytes to continuous growth in vitro (Biesinger et al. 1992). Thus, the two herpesviruses most homologous to KSHV have the ability to latently infect peripheral blood lymphocytes of their natural host, immortalize lymphocytes in vitro, and lead to the development of malignant lymphomas. This finding, in conjunction with the presence of KSHV sequences in all AIDS-BCBLs analyzed thus far, suggests that these sequences may play a pathogenic role in the development of some malignant lymphomas.

A need exists, therefore, to find means to isolate and propagate KSHV so that more can be learned about KSHV.

SUMMARY OF THE INVENTION

This need is met by the development of an in vitro model system suitable for the isolation and characterization of KSHV. The system is a cell line comprising KSHV, preferably a body cavity-based lymphoma (BCBL) cell line. The first model system is the BCBL cell line BC-2. Although very useful for several initial studies, this cell line, as well as nearly all KSHV$^+$ lymphomas described to date, falls short of the ultimate model system because of its concomitant infection with EBV. This invention thus also provides the establishment and characterization of a BCBL cell line that harbors KSHV in the absence of EBV and releases viral particles containing the KSHV genome. This cell line is designated BC-3 and will serve as an invaluable reagent for the characterization of the properties and functions of this novel, infectious agent KSHV.

Methods for propagating KSHV are also provided by the subject invention, by culturing the cell lines of the invention.

The invention further provides a purified viral suspension of KSHV, as well as a composition comprising purified KSHV and a suitable carrier.

DETAILED DESCRIPTION OF THE INVENTION

The subject invention provides a cell line which harbors or comprises Kaposi's sarcoma-associated herpesvirus (KSHV). Preferably, the cell line is a body cavity-based lymphoma cell line. One such cell line according to the subject invention is the cell line designated BC-2, which has been deposited with the ATCC as Accession No. CRL 2231. Another such cell line according to the subject invention is the cell line designated BC-3, which has been deposited with the ATCC as Accession No. CRL 2277. The cell line BC-3 harbors Kaposi's sarcoma-associated herpesvirus in the absence of Epstein-Barr virus.

Each of cell lines BC-2 and BC-3 have been deposited with the American Type Culture Collection (ATCC), 12301 Parklawn Drive, Rockville, Md. 20852, pursuant to and in satisfaction of the requirements of the Budapest Treaty on the International Recognition of the Deposit of Microorganisms for the Purposes of Patent Procedure. BC-2 was deposited on Oct. 23, 1995 as ATCC Accession No. CRL 2231 and BC-3 was deposited on Jun. 25, 1996 as ATCC Accession No. CRL 2277.

The invention further provides a method of propagating Kaposi's sarcoma-associated herpesvirus, the method comprising culturing the cell line (such as BC-2 or BC-3) of the invention. By culturing the cell line, the KSHV within the cell line thereby propagates. By culturing the cell line designated BC-3, the method allows for the propagation of KSHV in the absence of Epstein-Barr virus.

The BC-3 cell line thus allows for the purification of KSHV in the absence of EBV. The term "purified viral suspension" means a collection of KSHV viral particles (virions) in a liquid which is free or essentially free of other viruses, cells, or microorganisms and in which a substantial number of the viral particles are capable of causing an infection in a human host cell. The viral particles themselves may be recovered from the cell line and purified by techniques known in the art (see Example III). Purification of the recovered virus results in a purified viral suspension of the viral particles. The purified virus can be used to produce a composition comprising the purified KSHV and a suitable carrier known in the art. The purified viral suspensions of the subject invention can be useful reagents for research into the structure and function of KSHV.

In addition, the purified virus of the present invention can be used for diagnostic purposes, for example, for the detection of antibodies to the virus.

Such antibodies in fluids, tissues, or waste taken from a patient would indicate current or past exposure to the virus. The purified virus can also be used in tests of antiviral agents.

Purified virus may further be used for the production of specific antibodies, whether polyclonal or monoclonal, through known techniques. Such antibodies may be used for diagnostic and/or treatment purposes.

EXAMPLE I—BC-2

Pathologic Samples. The cell lines BC-1 and BC-2 were derived from previously reported cases lymphoma 1 and 2 (Cesarman et al. 1995a). Case 1 also corresponds to patient 1 reported by Chadburn et al. (Chadburn et al. 1993) and case 2 corresponds to patient 1 reported by Knowles et al. (Knowles et al. 1989). These cases also correspond to two of the three AIDS-related lymphomas found to be KSHV sequence-positive as reported by Chang et al. (Chang et al. 1994). The principal clinical, morphologic, immunophenotypic and genotypic characteristics of both cases have been reported (Cesarman et al. 1995a).

Malignant effusion samples were collected during the course of standard diagnostic procedures under sterile conditions. Mononuclear cells were isolated from the effusion samples by Ficoll-Hypaque (Pharmacia Fine Chemicals, Piscataway, N.J.) density gradient centrifugation. Cells were cryopreserved in liquid nitrogen in RPMI solution containing 10% dimethyl sulfoxide (DMSO) and 40% fetal calf serum at −170° C.

Establishment of Cell Lines and Cell Culture Procedures. The cryopreserved cells were thawed and plated at a concentration of $2 \times 10^6$/mL on top of a layer of heterologous feeder cells. For this purpose, peripheral blood lymphocytes from a normal donor were irradiated with 50 Gy and plated at a concentration of $1.5 \times 10^6$ per well in 24-well plates 24 hours before the addition of the lymphoma cells directly to these cultures. Because the AIDS-BCBL cells contain EBV, superinfection with this virus was not used for their establishment. Cells were grown in RPMI 1640 supplemented with 20% fetal bovine serum at 37° C. in the presence of 5% $CO_2$. Cell lines were passaged every 3 to 4 days after one to two cell doublings. Cell viability and evidence of cell lysis was evaluated by examination in a phase contrast microscope in the presence of Trypan blue.

Immunophenotypic Analysis. The immunophenotype of the BCBL tumor cells and cell lines was determined by direct and indirect immunofluorescent flow cytometry using the FACScan fluorescent activated cell sorter (Becton-Dickinson, Mountain View, Calif.) as previously described (Knowles et al. 1989; Walts et al. 1990; Chadburn et al. 1993). The monoclonal antibodies used include leukocyte common antigen (LCA; CD45), BerH2, Ki-1 (CD30), epithelial membrane antigen (EMA; Dako Corp, Santa Barbara, Calif.), B4 (CD19), B1 (CD20), B2 (CD21; Coulter Immunology, Hialeah, Fla.), Leu1 (CD5), Leu14 (CD22), Leu20 (CD23; Becton-Dickinson Immunocytometry Systems, Mountain View, Calif.) and T3 (CD3; United Biomedical Inc, Hauppauge, N.Y.). Antisera to kappa and lambda immunoglobulin light chains were obtained from Dako.

DNA Extractions. Genomic DNA was extracted from mononuclear cell suspensions by a previously reported salting-out procedure not requiring organic extraction (Miller et al. 1988). To determine the nuclear versus cytoplasmic localization of KSHV DNA, plasma membranes were disrupted by resuspending the cells in a solution of 20 mmol/L Tris (pH 7.9), 3 mmol/L $MgCl_2$, and 2 mmol/L $CaCl_2$, incubating 20 minutes on ice, and adding NP40 to 0.5%. The nuclei were then separated from the cytoplasmic fraction by centrifugation at 1,500 g for 15 minutes. The cytoplasmic fraction was recentrifuged at 2,500 g, and the pellet was discarded to eliminate residual nuclei. Subsequently, the microsomal fraction was separated from the cytoplasm by centrifugation at 17,000 g for 30 minutes. The three fractions—nuclear, microsomal, and cytoplasmic—were then extracted with phenol/chloroform. The method described by Hirt (Hirt 1967) was used to determine whether the KSHV DNA was of relatively high or low molecular weight. Essentially, the cells were lysed with 0.6% sodium dodecyl sulfate (SDS) and 1 mol/L NaCl; after centrifugation at 17,000 g for 30 minutes, the pellet containing the high-molecular-weight DNA was treated with Proteinase K, and both the pellet and supernatant were extracted with phenol/chloroform. Using this method, unintegrated small viral DNA molecules should be found in the supernatant.

Oligonucleotide Primers and Probes. All the oligonucleotides used for polymerase chain reaction (PCR) amplification in this study were synthesized by the solid-phase trimester method. Sequences of oligonucleotides used for amplification and sequencing of the $KS330_{233}$ region have been previously reported (Chang et al. 1994). Primers used for amplification and sequencing of flanking regions were derived from published sequences (Chang et al. 1994).

Direct Sequencing of PCR. PCRs were performed as previously described (Chang et al. 1994). DNA sequencing for the $KS330_{233}$ fragment and flanking region was performed on the two positive lymphomas from which the cell lines were obtained. PCR products were directly sequenced using the Taq DiDeoxy terminator cycle sequencing system with an ABI 373A automated DNA sequencer (Applied Biosystems Inc, Foster City, Calif.). The two strands and two independent PCRs were sequenced to exclude mismatches caused by polymerase mistakes.

Southern Blot Analysis. Aliquots (5 or 10 μg) of genomic DNA were digested with the appropriate restriction endonucleases according to the manufacturer's instructions (Boehringer-Mannheim, Indianapolis, Ind.), electrophoresed in 0.8% agarose gels, denatured with alkali, neutralized, and transferred to nitrocellulose filters according to Southern (Southern 1975). In cellular fractionation experiments, 1 μg of DNA from nuclear, cytoplasmic, and microsomal fractions was digested and loaded onto the corresponding lane; in the Hirt extraction experiments, 5 µg of DNA were used from both the pellet and the supernatant fractions. The filters were hybridized as previously described (Pelicci et al. 1985) to probes that had been $^{32}$P-labeled by the random primer extension method (Feinberg and Vogelstein 1983). Autoradiography was performed at -70° C. for 2 to 16 hours. The presence of KSHV sequences was determined by hybridization of BamHI-digested DNAs to $^{32}$P-labeled KS330Bam and KS631Bam probes (Chang et al. 1994). The immunoglobulin heavy chain gene was investigated by hybridization of EcoRI- and HindIII-digested DNAs to an immunoglobulin heavy chain gene joining region ($J_H$) probe (Korsmeyer et al. 1981). The presence and clonality of EBV was investigated by hybridization of BamHI-digested DNAs to a probe (TR) that detects EBV genomic termini (Raab-Traub and Flynn 1986).

In Situ Hybridization of Metaphase Spreads. Metaphase spreads were prepared from the BC-1 and BC-2 cell lines by conventional methods. For fluorescence in situ hybridization (FISH), a bacteriophage X clone, SGL1, containing a KSHV 12-kb insert was used as a probe. This clone was obtained by screening a lymphoma 1 genomic library with the KS631Bam fragment, and was shown to contain only KSHV sequences by hybridization experiments. SGL1 DNA was labeled by nick translation with biotin 11-deoxyuridine triphosphate (dUTP) (BRL, Gaithersburg, Md.). FISH and detection of the hybridized probe were performed as described (Mathew et al. 1992). Images were captured by a cooled CCD Camera (Photometrics, Tucson, Ariz.) and analyzed using Smartcapture Imaging System (Vysis, Framingham, Mass.).

Confirmation of KSHV Sequences in the AIDS-BCBL Tumor Cells. PCR amplification and sequencing of a 965-bp region of KSHV spanning the KS330Bam fragment was performed to confirm the presence and identity of these sequences in the tumor cells from cases lymphoma 1 and 2. The results show that the KSHV sequences in both of these cases are very similar to the sequence previously reported from a case of KS (Chang et al. 1994), differing by only three and 14 nucleotides in lymphomas 1 and 2, respectively. This result suggests that the sequences obtained by PCR from the malignant lymphomas correspond to the same agent previously identified in KS. Furthermore, some nucleotide differences were identified, consistent with the presence of independent isolates in the two lymphomas and the case of KS, making contamination unlikely.

Establishment of the BCBL Cell Lines. Two AIDS-BCBL cell lines were established from two different patients with lymphomatous effusions. These cell lines, BC-1 and BC-2, were derived from lymphoma cases 1 and 2, respectively (Cesarman et al. 1995a). The main characteristics of these neoplasms have been previously reported (Cesarman et al. 1995a). After cultures were started, only large tumor cells were visible at about day 30 in both cases. Both cell lines have a doubling time of 48 hours to 72 hours. Cells maintained at a concentration of $0.5 \times 10^6$/mL to $1.5 \times 10^6$/mL had a viability of greater than 80% and showed little evidence of lysis. Cells of both cultured BCBL cell lines tend to grow in small clusters. BC-1 and BC-2 cells have been grown for more than 150 and 50 passages, respectively.

Characterization of the BCBL Cell Lines.

Immunophenotypic analysis. Table 1 shows the results of the comparative immunophenotypic analysis performed on BC-1 and BC-2 cells and the original pathological specimens from which they were derived. These results demonstrate that the immunophenotype of the cell lines is generally comparable with the parental tumor. Once exception is the expression of CD23 by the original lymphoma 2 tumor cells but not by the BC-2 cells. Although the expression of CD23 was not studied in the lymphoma 1 tumor cells because of insufficient clinical material, it is not expressed in the BC-1 cells, similar to BC-2. CD23 is a B cell-associated activation antigen that is superinduced by EBV (Thorley-Lawson et al. 1985). The mechanism responsible for the loss of CD23 expression in these cell lines remains to be elucidated. The results of immunophenotypic analysis also show that the cultures contain a monotonous population of neoplastic cells, where over 99% of the cells were positive for the expressed antigens. Thus, methods such as limiting dilution to obtain pure cell populations were unnecessary.

Genotypic analysis. To define the clonality of the established BCBL cell lines and their derivation from the original neoplasm, Ig heavy chain gene rearrangement analysis was performed. Ten micrograms of DNA from a normal lymph node, used as a germline control, lymphoma 1 tumor cells, and BC-1 and BC-2 cell lines were digested with HindIII and hybridized to an Ig heavy chain joining region ($J_H$) probe. The normal lymph node showed a germline band at 11 kb, while the lymphoma 1 tumor cells, BC-1 cells, and BC-2 cells had clonal rearrangement bands. These studies demonstrated that BC-1 and BC-2 cells display clonal Ig gene rearrangements, which in BC-1 were identical to those seen in the corresponding pathologic specimen. Direct comparison of the Ig gene rearrangement pattern of BC-2 and the original tumor was not performed because of insufficient DNA from the latter. The cell lines and the original tumors were also studied for the presence and clonality of EBV. Five micrograms of DNA from a normal lymph node, used as a negative control, lymphoma 1 tumor cells, BC-1 cells, lymphoma 2 tumor cells, and BC-2 cells were digested with BamHI and hybridized to a DNA probe specific for the fused termini of the EBV genome. Both BCBL tumor cells and corresponding cell lines showed solitary strong bands, indicative of clonal EBV infection. The same pattern is seen in each of the cell lines as compared with the original tumor cells. Thus, EBV was present in both cell lines in similar copy number and with the same number of terminal repeats as in the original tumor cells. Thus, both cell line cultures contained the same clonal population as the tumor cells from which they were established.

Comparison of restriction pattern of KSHV in lymphoma 1 tumor cells, cell line, and KS. Southern blot analysis for KSHV sequences was performed using DNA obtained from the original BCBL-1 specimen and the cell line derived from this case to determine whether this virus is maintained with respect to copy number and structure in spite of multiple passages. DNA for these experiments was obtained from BC-1 cells after approximately 100 passages. BCBL-2 was not analyzed in the same manner because of insufficient DNA from the original tumor cells. DNA obtained from KS tissue was included in these studies as a control and to assess at this level the degree of identity of KSHV between KS and BCBL. Restriction enzyme analysis was performed with HindIII, Pst I, and Pvu II, after which agarose gel electrophoresis and transfer to nitrocellulose filters was performed. Filters were hybridized with $^{32}$P-labeled KS330Bam and KS631 Bam probes. The results demonstrated that although KSHV sequences were present in approximately 60-fold higher copy numbers in the lymphoma than in the KS DNA, the cell line had only slightly lower copy numbers than the original neoplasm. The restriction pattern was very similar when the BC-1 DNA was compared with the original tumor cells, except for a strong extra band in the cell line using Pst I restriction enzyme and the KS631Bam probe. This band may represent a polymorphism acquired in a proportion of the cells during passage. Other, fainter bands are seen with HindIII and probe KS330Bam in the original tumor cells, as well as with Pst I and KS330Bam in the cell line, which may be due to minor polymorphisms or partial DNA digestions (although the latter is unlikely as this experiment has been repeated with identical results). The restriction pattern is also very similar to that seen in the KS tissue, with the exception of the pattern seen with Pst I and probe KS627Bam and an additional band seen with Pvu II and probe KS330Bam, confirming once again the presence of a very similar, although not identical, organism.

Molecular Characterization of KSHV Sequences.

Nuclear versus cytoplasmic localization of KSHV sequences. To investigate the intracellular DNA localization of the KSHV sequences, DNA was isolated from nuclear, microsomal, and cytoplasmic fractions after cell lysis and centrifugation. The different fractions were digested with BamHI and analyzed by Southern blot hybridization with the KS330Bam probe. Most of the hybridization signal was seen in the nuclear fraction, suggesting that KSHV has a predominantly nuclear localization, a feature consistent with a herpesvirus. As a control, the same filters were rehybridized with a probe for EBV, and the hybridization signal was similarly obtained in the nuclear fraction.

Hirt extraction of KSHV DNA. A method for selective extraction of low-molecular-weight DNA was established by Hirt (Hirt 1967) to purify polyoma virus DNA. Hybridization to the KS330Bam probe occurred predominantly in the pellet, containing the high-molecular-weight DNA fraction, and only fainter hybridization is seen in the supernatant, containing the low-molecular-weight DNA. Similar results were obtained when these filters were rehybridized with a probe for EBV. These results suggest that most of the KSHV DNA is either integrated or of a relatively large size.

In situ hybridization of metaphase spreads. In situ hybridization of metaphase spreads prepared from the BC-1 and BC-2 cells was performed to determine whether the KSHV sequences were integrated or episomal. No specific integration site was identified, consistent with episomal DNA. In addition, multiple signals were detected in each cell, consistent with previous quantitative data suggesting that 40 to 80 copies of KSHV are present per cell in AIDS-BCBLs (Cesarman et al. 1995a).

This example describes the in vitro establishment of two AIDS-BCBL cell lines, BC-1 and BC-2. AIDS-BCBLs represent a clinicopathologically distinct subset of AIDS-related malignant lymphomas that, among other distinguishing features, are characterized by the presence of KSHV sequences (Cesarman et al. 1995a). The similarity of these cell lines to the tumor cells from which they were derived has been demonstrated by immunophenotypic and immunogenotypic studies. An important feature of the AIDS-BCBL cell lines is the retention of essentially unchanged KSHV sequences in spite of numerous passages.

The BCBL cell lines were used to assess whether the genomic structure of the KSHV sequences is consistent with previous sequence homology data suggesting they belong to a herpesvirus. Although the human herpesviral genomes range in size from 120 to 230 kilobase pairs and are linear and double-stranded, they circularize immediately after release from capsids into the nuclei of infected cells. Thus, although herpesvirus DNA can sometimes integrate into the mammalian genome, it is usually found as nuclear circular episomes in latently infected cells (Roizman 1990). KSHV sequences are present predominantly in the nucleus. Furthermore, these sequences were largely absent from Hirt supernatants. Although this method was established for selective extraction of low-molecular-weight DNA (Hirt 1967), it has also been used to extract herpesvirus DNA, including that of herpes simplex virus (Pater et al. 1976), herpes zoster virus (Rapp et al. 1977), and human cytomegalovirus (Rosenthal et al. 1983), despite their relatively large size. However, only unit-size linear herpesvirus DNA molecules, present in productive infections, have been found in the Hirt supernatants. In contrast, larger replicative structures are retained with the cellular DNA when using this method (Ben-Porat et al. 1976). Thus, the scarcity of KSHV DNA in the Hirt supernatants suggests a latent infection by a large, or integrated, viral genome, with a small amount of either mature linear viral DNA or fragmented DNA caused by cellular lysis. The in situ hybridization of metaphase spreads demonstrated KSHV sequences in episomal structures. Thus, KSHV sequences are present as large nuclear episomes in the BCBL cell lines, consistent with a latent herpesvirus genome.

The two established AIDS-BCBL cell lines retain the KSHV sequences present in the parental tumor cells (Cesarman et al. 1995a). These cells represent an important biologic reagent for further characterization of the nature of these sequences. The AIDS-BCBL cell lines should provide a great aid in future experiments aimed at determining whether this putative virus has transforming capabilities and its role in the development of KS as well as a subset of AIDS-related NHLs.

EXAMPLE II—BC-3

Pathologic samples, cell line establishment, and cell culture. The BC-3 cell line was established from a lymphomatous pleural effusion sample collected from a human immunodeficiency virus-negative (HIV) patient previously reported in the literature (Nador et al. 1995). Mononuclear cells were isolated from the effusion samples by Ficoll-Hypaque (Pharmacia Fine Chemicals, Piscataway, N.J.) density gradient centrifugation. Viable cells were plated at a concentration of $2 \times 10^6$/mL onto a layer of heterologous feeder cells as previously described (Cesarman et al. 1995b). Cells were maintained in RPMI 1640 supplemented with 2 mmol/L glutamine and 20% fetal bovine serum at 37° C. in the presence of 5% $CO_2$. After approximately 4 weeks in culture, the feeder cells progressively disappeared compared with control plates, giving way to a proliferating cell population. The cells from this well were progressively expanded, passaged every 3 to 4 days, and seeded at 0.3 to $0.5 \times 10^6$/mL (cell viability was evaluated by Trypan blue exclusion). BC-1 and BC-2 cells (see Example I) were used as controls for the presence of KSHV and EBV genomes in the present studies.

Immunophenotypic analyses. The immunophenotype of the BCBL and the BC-3 cell line were determined by direct and indirect immunofluorescent flow cytometry using a FACScan fluorescent activated cell sorter (Becton Dickinson Immunocytometry Systems, Mountain View, Calif.) as previously described (Knowles et al. 1989; Walts et al. 1990; Chadburn et al. 1993). The monoclonal antibodies (MoAbs) used included BerH2 (CD30; Dako Corp, Santa Barbara, Calif.), B4 (CD19), B1 (CD20), B2 (CD21), CALLA (CD10; Coulter Immunology, Hialeah, Fla.), Leu1 (CD5), Leu14 (CD22), Leu20 (CD23), Leu9 (CD7), LeuM3 (CD14), Ia (HLA-DR), T4 (CD4), T8 (CD8), My10 (CD34), T11 (CD2), IL2R (CD24), ICAM (CD54), G28-5 (CD40; Becton Dickinson), T3 (CD3; United Biomedical Inc, Hauppauge, N.Y.) and T9 (CD71), T10 (CD38; Ortho, Raritan, N.J.). Antisera to total Ig, kappa ($\kappa$) and lambda ($\lambda$) Ig light chains were obtained from Dako.

DNA extraction, Southern blot analyses. Genomic DNA was extracted by a salting-out procedure as previously described (Miller et al. 1988). Aliquots (5 mg) of genomic DNA were digested with appropriate restriction endonucleases as per the manufacturer's instructions (Boehringer Mannheim, Indianapolis, Ind.), size-fractionated by electrophoresis in 0.8% agarose gels, denatured (1.5 mol/L NaCl, 0.5 mol/L NaOH), neutralized (0.5 mol/L Tris pH 7.4, 3 mol/L NaCl), and transferred to nitrocellulose filters as per Southern (Southern 1975). Filters were then hybridized appropriately with $\alpha$-$^{32}$P(dCTP) random prime-labeled (PrimeIt II; Stratagene, La Jolla, Calif.) DNA probes for the Ig heavy-chain joining region ($J_H$), the T-cell receptor $\beta$-chain, the c-myc oncogene, KSHV (KS330Bam and KS631Bam fragments) (Chang et al. 1994), or EBV (terminal repeat region) (Raab-Traub and Flynn 1986) as described previously (Pelicci et al. 1985).

Polymerase chain reaction (PCR) conditions, oligonucleotide primers, and probes. Total RNA was isolated using the Tri-Reagent nucleic acid extraction method (Molecular Research Center Inc, Cincinnati, Ohio) according to the manufacturer's instructions. To eliminate contaminating genomic DNA, the RNA samples were treated with 2 U RNase-free DNaseI (Boehringer Mannheim), with subsequent heat-inactivation of the enzyme. RNA-based PCR was performed on 1 mg RNA using the Superscript Reverse Transcriptase System (GIBCO-BRL, Grand Island, N.Y.) according to the manufacturer's instructions. PCR reactions were also performed on RNA samples without the reverse transcription step to control for amplification due to genomic DNA contamination. PCR conditions, and sequences of oligonucleotides used for the amplification and hybridization of both the KSHV KS330$_{233}$ Bam fragment and its flanking sequences, were as originally reported (Chang et al. 1994; Cesarman et al. 1995b). Primers and probes for EBV included sets for the EBNA-2, EBNA-3C, and EBER regions, the first two allowing the accurate distinction of both types A and B EBV (Lin et al. 1993). Oligo sequences and PCR conditions for these EBV regions were as previously published (Frank et al. 1995). All oligonucleotides used in these studies as PCR primers or probes were obtained commercially (GIBCO-BRL). PCR primers and probes for the KSHV open reading frames or ORFs were as follows: (1) for ORF 75 (membrane antigen homolog), 5' primer: SEQ ID NO:1: 5'-AGGAGCGAGAGAGACGGGAT-3', 3' primer: SEQ ID NO:2: 5'-CCAGGTGCCTGCCCACTTCC-3' and probe: SEQ ID NO:3: 5'-CCTAGCTCTTGCAGCAGA-AC-3'; (2) for ORF 74 (G-protein coupled receptor homolog), 5' primer: SEQ ID NO:4: 5'-CGGGGTGCCTTACACGTGG-3', 3' primer: SEQ ID NO:5: 5'-CAGTCTGCAGTCATGTTTCC-3' and probe: SEQ ID NO:6: 5'-TGTGTGCGTCAGTCTAGTGAG-3'; (3) for ORF 73, 5' primer: SEQ ID NO:7: 5'-GCAGTCTCCAGAGTCTTCTC-3', 3' primer: SEQ ID NO:8: 5'-CGGAGCTAAAGAGTCTGGTG-3' and probe: SEQ ID NO:9: 5'-TGGAGGTGTAGTCTGCTGCG-3'; (4) for ORF 72 (cyclin D homolog), 5' primer: SEQ ID NO:10: 5'-CACCCTGAAACTCCAGGC-3', 3' primer: SEQ ID NO:11: 5'-GATCCGATCCTCACATAGCG-3' and probe: SEQ ID NO:12: 5'-CGCCACTCTATATGCAAACTG-3'. A primer set specific for the human $\beta$-actin cDNA (Stratagene) was used as a quantitative control. Because this primer set spans an intron, it can only amplify sequences that have derived from reverse-transcribed RNA and not from contaminating DNA, thus serving as an ideal positive control. The sequence of the $\beta$-actin internal oligonucleotide probe was: SEQ ID NO:13: 5'-GGATGTCCACGTCACACTTC-3'. PCR reaction products (m-mL aliquots) were fractionated by electrophoresis and transferred to nitrocellulose filters as described above for genomic DNA Southerns. Filters were hybridized with oligonucleotide probes for KSHV and EBV that were end-labeled with $\gamma$-$^{32}$P(dATP) using T4 Polynucleotide Kinase (Boehringer Mannheim). The similar melting temperatures of the EBV oligonucleotide probes allowed their simultaneous hybridization to the nitrocellulose filter. Furthermore, direct sequencing of PCR products from the KS330 Bam region and flanking sequences for the purpose of verification was performed as previously described (Cesarman et al. 1995b).

Pulsed-field gel electrophoresis (PFGE). Cells ($25\times10^6$/mL final), viral pellets from culture supernatants or cellular fractions (see below) were molded into agarose plugs using 1% LMP agarose (Bio-Rad, Richmond, Calif.) and 0.9% NaCl. Plugs were incubated 2×24 hours at 50° C. in lysis buffer consisting of 0.5 mol/L EDTA pH 8.0, 1% Sarkosyl, 1 mg/mL Proteinase K (GIBCO-BRL), washed, and stored in 0.5 mol/L EDTA at 4° C. until ready for use. PFGE was performed using a CHEF-DR II System (Bio-Rad) per the manufacturer's instructions. Samples were run on 1% PFGE-certified agarose (Bio-Rad) gels in 0.5×TBE at 200 V, ramped from 3 to 30 seconds for 23 hours at 14° C., with constant buffer recirculation using a peristaltic pump. Molecular-weight marker plugs were obtained commercially (PFGE Marker I-1 Ladder; Boehringer Mannheim). Gels were transferred to nitrocellulose filters and probed successively with radiolabeled DNA probes for KSHV and EBV as described above.

Viral isolation and negative staining electron microscopy. Viral pellets were prepared as previously described (Mesri et al. 1995). Briefly, BC-1 or BC-3 cells were collected by centrifugation for 10 minutes at 1,500 rpm, resuspended in 1:20 vol of culture medium, and snap-frozen (cell virus extract). Supernatant virus was obtained by centrifugation of a 1,400 g-cleared conditioned culture medium for 2 hours at 23,000 g at 4° C. Pellets were then resuspended in 1:50 vol of culture medium and snap-frozen. Both preparations (cell or supernatant virus) were then thawed, sonicated in a cup sonicator (Heat Systems, N.Y.), cleared by centrifugation at 10,000 g at 4° C., loaded on a phosphate-buffered saline (PBS)-25% sucrose cushion, and pelleted by overnight centrifugation at 70,000 g at 4° C. Finally, viral pellets were resuspended in PBS and either embedded in agarose for pulsed-field electrophoresis or adsorbed onto parlodion/carbon-coated grids using the agar diffusion method, stained with 2% phosphotungstic acid (pH 6.8) and examined with a JEOL electron microscope.

Morphologic and immunopheno typic characterization. The BC-3 cells were large and contained abundant basophilic cytoplasm, occasionally with a paranuclear hof, and large round to polygonal and sometimes pleomorphic nuclei with one or more prominent nucleoli. These morphologic features are consistent with their classification as a BCBL. This classification is further consolidated by immunophenotypic analyses that showed that BC-3 cells express CD45, but do not express B-cell lineage-restricted antigens (CD19, CD20, CD21, CD22, $\kappa$ or $\lambda$ Ig light chains) or T-cell lineage-restricted antigens (CD2, CD3, CD4, CD5, CD8). There was variable expression of activated antigens, with expression of CD30, CD38, CD54, CD71, and HLA-DR.

Genotypic characterization. To determine the lineage and clonality of these cells, several genomic markers were investigated by Southern hybridization. DNA from HL60 cells was used as a negative control for gene rearrangement, based on previous knowledge that this cell line has a germline configuration of the genes examined by the $J_H$, $T_\beta$, and c-myc probes, even though the c-myc gene is amplified and gives a stronger hybridization signal. Restriction endonuclease digestion of genomic DNA and subsequent hybridization to appropriate radiolabeled probes showed that BC-3 cells have rearranged Ig heavy chain as well as κ and λ light-chain genes, and retain the germline configuration for the $T_\beta$ genes, indicating a clonal B-cell population. The c-myc proto-oncogene is also in its germline configuration, further consolidating classification as a BCBL. Direct comparison of Southern hybridization analyses for Ig genes between DNA from the original tumor samples and DNA from the BC-3 cell line corroborated the tumor derivation of this cell line.

Presence of viral sequences in BC-3 cells. PCR analyses on genomic DNA from the original tumor sample suggested the presence of KSHV sequences in the absence of EBV and HIV (Nador et al. 1995). Preliminary Southern blot hybridization analyses on genomic DNA from both the original tumor and the BC-3 cells also suggested the presence of KSHV in the absence of EBV sequences. In addition, in situ hybridization for EBER was negative. To further evaluate the viral genomes present in the BC-3 cells, the presence of KSHV and EBV sequences in these cells was examined by PCR. A panel of three EBV genes was used, namely EBNA-3C, EBNA-2, and EBER, to detect both type A and B forms of EBV and to exclude the possibility of false negatives arising as a result of the presence of mutant EBV genomes with deleted sequences. As controls, two other BCBL cell lines were used, namely BC-1 and BC-2 (see Example I), both of which are known to be positive for KSHV, and EBV types B and A, respectively (Cesarman et al. 1995b). PCR analyses showed that BC-3 cells, like BC-1 and BC-2, are positive for KSHV as judged by the presence of sequences from the KSHV330 fragment. However, and in contrast to BC-1 and BC-2 cells, BC-3 cells are negative for EBV as shown by the absence of hybridization signals with the EBNA-3C, EBNA-2, and EBER probes. To confirm the KSHV origin of these amplification products, a 1,110-bp region containing the originally described 233-bp fragment as well as 492 bp upstream and 385 bp downstream flanking sequences (Chang et al. 1994; Cesarman et al. 1995b) was sequenced. The sequences of the amplified fragments were identical to the previously reported KSHV sequence derived from a KS specimen (Chang et al. 1994), except for nine altered bases at positions 683 (T→C), 686 (T→C), 981 (T→C), 1032 (C→A), 1033 (C→T), 1055 (G→T), 1132 (A→G), 1139 (A→C), and 1514 (G→A), which fall within the variation expected among different isolates. BC-3 cells are also negative for other herpesviruses such as herpes simplex virus types 1 and 2 (HSV-1 and HSV-2) and cytomegalovirus as determined by immunohistochemistry analyses.

Expression of KSHV sequences in BC-3 cells. In an attempt to characterize the biologic significance of the presence of KSHV sequences in the BC-3 cell line, an RNA-based PCR assay was used to analyze the expression of four KSHV ORFs previously identified in the region surrounding the originally reported KS631 Bam fragment (Chang et al. 1994). These ORFs include a cyclin D homolog, a G-protein coupled receptor homolog, a homolog of HVS ORF 75 which is thought to encode a tegument protein, and the positional homolog of HVS ORF 73 whose function is unknown. All four ORFs were found to be expressed as determined by RNA-based PCR analyses, suggesting that these KSHV sequences are part of a functional viral genome rather than spurious DNA sequences. PCR on RNA samples lacking the reverse transcription step failed to yield any amplification products, thus confirming that the observed fragments did not arise from genomic DNA contamination.

Characterization of KSHV particles in BC-3 cells. To show the presence of KSHV particles in the BC-3 cells, the genomic DNA content was analyzed by PFGE. As before, the BC-1 and BC-2 cell lines provided useful controls for the presence of KSHV and EBV genomes. The BC-1 cells show a band at about 270 kb, as previously reported (Moore et al. 1996). In contrast, the BC-2 and BC-3 cells when hybridized with a KSHV probe show bands of approximately 200 and 180 kb, respectively. This difference is highly reproducible, and does not stem from technical or experimental variables. Viral pellets obtained from BC-3 cellular or supernatant fractions show a band of 170 kb, at the same position as that of the bands in the BC-3 cells. As expected, a band at the appropriate molecular weight was identified with an EBV probe in the P3HR1 and Raji control cell lines and in the BC-1 and BC-2 cell lines, but was absent from the BC-3 cell line.

Previous attempts to directly visualize KSHV particles have been obscured by the concomitant presence of EBV in all biologic samples and established cell lines thus far examined. However, the BC-3 cell line is ideally suited for the examination of KSHV particles at the electron microscopic level. Negative staining electron microscopy showed the presence of viral capsids of approximately 100 to 150 nm diameter. Although the two capsids were collapsed, ring-shaped capsomers of approximately 9-nm diameter arranged in linear arrays were discernible. Some of these capsomers clearly showed up as hexons whereas others in the periphery appeared as hollow tubes giving a castellated edge. These features are characteristic of herpesviruses and herpesviral preparations (Madeley and Field 1988). Taken together with the PFGE analyses, these results indicate that BC-3 cells are infected with KSHV and release KSHV particles.

This example describes the establishment and characterization of a cell line, BC-3, which is shown by immunophenotypic and genotypic analyses to belong to a rare group of malignancies termed BCBL or primary effusion lymphomas. BC-3 cells are of B-cell origin as judged by their clonal Ig heavy- and light-chain gene rearrangements and germline T-cell receptor genes. In line with all previous published cases of BCBL, the BC-3 cells are positive for KSHV sequences; however, the novelty of this cell line lies in the absence of EBV coinfection as determined by Southern hybridization, in situ hybridization, PCR, and PFGE analyses. This cell line consequently provides an opportunity to isolate, characterize, and functionally dissect the recently discovered KSHV.

The first report of the KSHV sequences as detected in KS tissues (Chang et al. 1994) raised questions regarding the nature of these sequences and the evidence for a bona fide viral particle. Sequencing and formal phylogenetic analyses of large portions of the KSHV genome have demonstrated that it is a γ-2 herpesvirus (genus Rhadinovirus), and the first member of this group to infect humans (Moore et al. 1996). Furthermore, with the establishment of the BC-1 and BC-2 cell lines (Cesarman et al. 1995b) (Example I), it became possible to visualize the KSHV DNA by PFGE analyses as well as to perform transmissibility studies to prove that these sequences belong to a functional virus capable of infecting cells and replicating in them (Moore et al. 1996). According to these studies, the KSHV genome in the BC-1 cell line has a molecular weight of approximately 270 kb. The data presented in this report confirm these findings, yet also show KSHV particles of lower molecular weight in the BC-2 and BC-3 cell lines. The molecular weight of the KSHV genomes in the BC-3 cells and viral isolates is approximately 170 kb, and this is a highly reproducible finding not attributable to technical or experimental variations. Because the viral preparations were extensively sonicated before PFGE and Southern analyses, the fact that sharp bands were obtained corresponding to intact genomes for BC-1 and BC-3 viral isolates is an indication that these genomes are protected from sonication, and therefore evidence for their encapsidation. Moreover, KSHV DNA fragments are protected from DNase degradation, further suggesting that these viral isolates contain encapsidated genomes. Viral isolates obtained from the BC-1 cell lines are capable of infecting umbilical cord blood B cells. Furthermore, KSHV transmission is blocked by UV-irradiation and foscarnet (an inhibitor of viral DNA-polymerase), thus providing evidence for the presence of a biologically active virus. Similarly, viral isolates from BC-3 cells appear to infect cell lines of the B-cell lineage.

Although the precise explanation and significance of the differences in genomic size among various KSHV isolates can only be addressed when a physical map of the virus becomes available, these particles do correspond to KSHV based on the presence and sequence analyses of the KS330 Bam fragment, which is thus far the single available criterion for detecting the presence of this virus. Further evidence that the sequences present in BC-3 cells correspond to KSHV is provided by our RNA-based PCR assays, which detected and amplified fragments from four different ORFs derived from a region very distant from the KS330 Bam fragment. Expression of these four ORFs further suggests that this virus is functional and has an active biologic role in these BCBL cells. The homologies of these ORFs to genes involved in cell cycle regulation raise interesting questions as to their potential role(s) in viral transformation and/or pathogenesis. For example, ORF 72, a cyclin D homologue, may be involved in the subversion of the host cell cycle to the advantage of viral replication. In this respect, HVS contains an ORF that encodes a viral cyclin D homologue capable of interacting with host-cell cyclin-dependent kinases and thus potentially playing a role in the oncogenic transformation process (Jung et al. 1994). Although EBV lacks a cyclin D homologue, its latent membrane protein-1 (LMP-1) has been shown to upregulate the expression of cellular cyclin D2 leading to the loss of transforming growth factor-β1-mediated growth inhibition and perhaps contributing to cellular transformation (Arvanitakis et al. 1995).

Finally, electron microscopic examination of the viral preparations showed the presence of viral particles having the morphologic features typical of herpesviral capsids, and particularly those of gammaherpesviruses (Madeley and Fields 1988), suggesting that they may correspond to KSHV. These results are in agreement with transmission electron microscopy studies performed on KSHV+ cells obtained from the same patient as the BC-3 cells but after passage in BNX mice. Besides being an invaluable tool for the isolation and characterization of KSHV, the BC-3 cell line provides an opportunity to investigate the pathogenesis of BCBL. An expanded cytogenetic and immunophenotypic analysis of these cells may yield clues as to the nature of the B lymphocyte which is infected by KSHV and perhaps point to the cell surface molecule(s) acting as the viral receptors. In summary, BC-3 cells will serve as a tool which will allow us to address the more significant questions regarding the role(s) of KSHV in the pathogenesis of BCBL, KS, and multicentric Castleman's disease.

EXAMPLE III—Isolation of KSEV from BC-1

Herpesviral DNA fragments from AIDS-associated Kaposi's sarcoma (KS) tissue (KSHV-DNA) share homology with two lymphotropic oncogenic γ-herpesviruses, Epstein-Barr virus and Herpesvirus saimiri, and are present in the lesions of more than 95% of HIV and non-HIV-associated forms of KS, AIDS-related body cavity-based lymphomas, and AIDS-related multicentric Castleman's disease. BC-1, a KSHV-DNA-positive, body cavity-based lymphoma cell line, produces infective herpesviral particles carrying a linear 270-kb genome that specifically transmits KSHV-DNA to CD19+ B cells. Transmission of KSHV-DNA is dependent upon a biologically active, replicating virus, since it is blocked by UV irradiation and foscarnet, an inhibitor of viral DNA-polymerase. This study represents the first isolation and transmission of the human herpesvirus-8/KS-associated herpesvirus.

Viral Preparation. Viral pellets were obtained as described in Dixon and McLauchlan (1993). Briefly, BC-1 cells (Cesarman et al. 1995b) were collected at low-speed centrifugation, resuspended in 1:20 vol of media, and snap-frozen (cell-associated virus extract). To obtain supernatant virus pellets, postculture-conditioned media from BC-1 cells was cleared by centrifugation at 1,400 g 4° C. filtered through a 0.45-μm membrane and centrifuged 2 h at 23,000 g at 4° C. Pellets were resuspended in 1:50 vol of media and snap-frozen in dry ice/ethanol. Both extracts (cell or supernatant virus) were thawed and frozen and thawed once more, sonicated 4×40 s in a cup sonicator (Heat Systems-Ultrasonics, Inc., Plainview, N.Y.), and cleared by centrifugation at 10,000 g at 4° C. To concentrate and further purify the viral preparations (Federoff et al. 1992), they were loaded over a 25% sucrose/PBS ($Ca^{2+}$, $Mg^{2+}$) cushion and pelleted by overnight centrifugation at 70,000 g at 4° C. Viable BC-1 cells that might contaminate the preparation were excluded by passaging through a 0.45-μm filter (supernatant virus), triple freezing and thawing in the absence of freezing agents, and extensive sonication and centrifugation at 10,000 g. Furthermore, the viral isolates were examined for the presence of any contaminating cell by light and electron microscopy, by culture in rich medium, and sensitivity to DNAse degradation of the cellular gene p53 matched with a control of viable BC-1 cells.

Negative-staining. Electron Microscopy. Viral pellets were resuspended in PBS ($Ca^{2+}$, $Mg^{2+}$), and the virus was absorbed onto parlodion/carbon-coated grids using the agar diffusion method, stained with 2% phosphotungstic acid, pH 6.8, and viewed with an electron microscope (JEOL U.S.A. Inc., Peabody, Mass.).

Pulse Field Gel Electrophoresis (PFGE) Analysis. Cells ($25 \times 10^6$/ml final) or cell viral pellets (corresponding to $2 \times 10^8$ cells) were molded into 0.9% NaCl low melting point agarose plugs. The plugs were incubated for 2 d at 50° C. in lysis buffer (0.5 M EDTA, pH 8.0, 1% sarkosyl, 1 mg/ml proteinase K), and washed and stored in 0.5 M EDTA at 4° C. PFGE was performed using a CHEF-DR II system (Bio Rad Laboratories, Richmond, Calif.) following the manufacturer's instructions. Samples were run on 1% PFGE-certified agarose (Bio Rad) gels in 0.5 X Tris-borate-EDTA buffer at 200 V, initial A time=3s, final A time=30s, for 23 h at 14° C. PFGE Marker I ladder molecular weight marker plugs were obtained from Boehringer Mannheim Biochemicals (Indianapolis, Ind.).

Southern Blot for KSHV-DNA or EBV Sequences. Gels were transferred to nitrocellulose filters and probed with random prime $^{32}$P-labeled probes for KSHV-DNA (KSBam330 fragment [Chang et al. 1994]) or the EBV terminal repeat region (Cesarman et al. 1995a; Cesarman et al. 1995b).

PCR Detection of KSHV-DNA and p53. Cells were pelleted and resuspended in 3 μl PBS. Resuspended cells, or viral extracts (3 μl), were treated with 30 μl of Genereleaser (Bio-Ventures, Mufreesboro, Tenn.). The DNA was released in a thermocycler following the manufacturer's protocol. Primers for KSBam 330233 or for p53 (Chang et al. 1994) were added to one third of the DNA, and a PCR reaction was carried out in a thermocycler as described (Chang et al. 1994).

DNAse Treatment of the Viral Isolates. Before PCR, viral extracts were treated with RNAse-free DNAse I (Boehringer Mannheim) for 15 min following the manufacturer's conditions.

Infection Studies. Umbilical cord blood mononuclear cells (CBMC) obtained by Ficoll centrifugation were incubated for 40 min at room temperature with viral extracts at a cell density of $10^7$ cells/ml, washed once with media to remove excess virus, resuspended in RPMI, 20% FCS, 20% CD34-derived spindle cell conditioned media (RC-20 medium) at a density of $10^6$ cells/ml, and incubated during a week. For PCR, one-third of the cells were harvested, washed once with media, and treated with Genereleaser.

UV Irradiation of the Viral Preparations. Viral pellets resuspended in PBS or media were exposed to a dose of 9 mJ of UV light using a Stratalinker (Stratagene, La Jolla, Calif.).

Enrichment in CD19 Cells and Immunodepletion of CD19 Cells. B cells were immunoselected from CBMC using an anti-CD19 mAb coupled to magnetic beads (Dynabeads; Dynal, Lake Success, N.Y.) following the manufacturer's conditions. A similar procedure repeated three times was used to deplete the CBMC of B cells.

Effect of Foscarnet. Infected cells were incubated in the presence of different doses of Foscarnet (Foscavir; Astra, Westborough, Mass.).

Methods for herpesviral preparation and concentration were used to obtain viral particles from BC-1 cells, an AIDS-related, body cavity-based lymphoma (BCBL) cell line that stably carries KSHV-DNA (see Example I). Sucrose cushion purified cell-free pellets were obtained (see above) that were KSHV-DNA-positive by PCR from both BC-1 cells and their supernatants. KSHV-DNA present in the viral preparations within a viral capsid should be resistant to DNAse degradation, whereas free DNA should be sensitive. As an internal control for free (nonencapsidated) DNA in a DNAse sensitivity assay of KSHV-DNA from viral isolates, the detection of the cellular gene p53 was used, present in free BC-1 cellular genomic DNA which is also found in the viral preparations. When the pellets were treated with DNAse, the p53 gene could no longer be detected by PCR. In contract, the KSHV-DNA in the viral isolates is DNAse resistant and can be amplified by PCR after DNAse treatment, indicating that the KSHV-DNA is protected, quite possibly inside a viral capsid. To show that DNAse protection of viral genes was not limited to this KSHV-DNA fragment (KS330Bam) and its immediately adjacent region, a similar analysis with a viral gene adjacent to the other reported KSHV fragment (KS631Bam, Chang et al. 1994) was also carried out. This KSHV gene was also protected from DNAse degradation.

To further characterize the viral preparation, negative-staining electron microscopy was performed that showed the presence of several virus-like particles. While none of these particles allows unequivocal identification as a herpesvirus, they have features of the herpesviruses and similarly appearing particles are characteristic of herpesviral preparations (Madeley and Field 1988). No intact cells or other cellular organelles were seen in these preparations.

PFGE of the viral preparations showed that KSHV-DNA belongs to a linear 270-kb genome present both in BC-1 cells (Moore et al. 1996) and in the viral pellet. In contrast, EBV, also produced by BC-1 cells (Cesarman et al. 1995b), hybridizes with a 170-kb genome. Results show that in the BC-1 viral isolates, KSHV-DNA is contained in a viral genome that is distinct from the EBV genome. The DNAse protection of distant segments of the 270-kb KSHV-DNA viral genome, in contrast with the DNAse sensitivity of nonvirally associated genes and the presence of herpesviral-like particles in the isolates, are consistent with encapsidation of the KSHV-DNA viral genome.

To determine whether the virus carrying KSHV-DNA was infective, the viral preparations were tested for their capacity to infect CBMC. Viral transmission of KSHV-DNA to CBMC after 1 wk of exposure to the viral isolates was tested. UV irradiation of the viral extracts abolished KSHV-DNA transmission without modifying its ability to act as a PCR template. Since this dose of UV irradiation is known to inactivate herpesviral DNA replication and transcription, the results indicate that transmission of KSHV-DNA is accomplished by transmission in an active herpesvirus, HHV-8/KSHV.

A recent report notes that KSHV-DNA is not present in AIDS-KS spindle cell lines, but is found in the CD19 B cell compartment of KS patients (Ambrosziak et al. 1995). This finding and the fact that KSHV-DNA is present in the neoplastic cells of BCBL (Cesarman et al. 1995a; Cesarman et al. 1995b) strongly suggest that HHV-8/KSHV may be a lymphotropic virus possibly targeting the B cell compartment. To establish whether HHV-8/KSHV is a B cell-specific virus, immunoselection techniques were used to positively select CD19$^+$ (Pan-B) cells from cord blood and to deplete cord blood mononuclear cells of CD19$^+$ cells. The results show that the preselected CD19-positive CBMCs were infectable with KSHV, while CD19-depleted CBMC were not infected. These results indicate that HHV-8/KSHV is a B-lymphotropic herpesvirus.

Foscarnet is a specific inhibitor of herpesviral DNA polymerase (Crumpacker 1992). Its potential benefit as a therapeutic agent for AIDS-KS may be of importance (Morfeldt and Torssander 1994; Jones et al. 1995). The results show that foscarnet has an inhibitory effect on the transmission of KSHV-DNA to CBMC, further reinforcing the concept that transmission and persistence of KSHV-DNA depends on a replication-competent herpesvirus.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Summary of Immunophenotypic Profiles of Two AIDS-BCBLs and the Corresponding Cell Lines

| Antigen | Lymphoma 1 Tumor Cells | BC-1 Cell Line | Lymphoma 2 Tumor Cells | BC-2 Cell Line |
|---|---|---|---|---|
| CD45 | >90 | >99 | >90 | >99 |
| CD19 | — | — | — | — |
| CD20 | — | — | — | — |
| CD21 | — | — | — | — |
| CD22 | — | — | — | — |
| CD23 | ND | — | >90 | — |
| Ig | — | — | — | — |
| CD3 | — | — | — | — |
| CD5 | — | — | — | — |
| CD30 | >90 | >99 | — | — |
| EMA | >90 | >99 | ND | >99 |

If positive, the percentage of positive cells is given; —, negative.
Abbreviations: EMA, epithelial membrane antigen; ND, not determined.

REFERENCES

Albrecht, J. C., et al., J Virol 66:5047 (1992).
Ambrosziak, J. A., et al., Science 268:582–583 (1995).
Arvanitakis, L., et al., J Immunol 155:1047 (1995).
Baer, R., et al., Nature 310:207 (1984).
Ballerini, P., et al., Blood 81:166 (1993).
Ben-Porat, T., et al., Virology 69:547 (1976).
Biesinger, B., et al., Proc Natl Acad Sci USA 89:3116 (1992).
Cesarman, E., et al., N Engl J Med 332:1186–1191 (1995a).
Cesarman, E., et al., Blood 86:2708–2714 (1995b).
Chadburn, A., et al., Cancer 72:3078 (1993).
Chang, Y., et al., Science 266:1865–1869 (1994).
Crumpacker, C. S., Am J Med 92:2A3S-2A7S (1992).
Dixon, F. J. and McLauchlan, J., in Davison, A. J. and Elliot, R. M. (eds), *Molecular Virology,* IRL Press, Oxford, New York (1993) pp. 285–307.
Federoff, H. J., et al., Proc Natl Acad Sci USA 89:1636–1640 (1992).
Feinberg, A. P. and Vogelstein, B., Anal Biochem 132:6 (1983).
Fleckenstein, B. and Desrosiers, R. C., in Roizman, B. (ed), *The Herpesviruses,* Plenum Press, New York, N.Y. (1982) p. 253.
Frank, D., et al., Blood 85:1396 (1995).
Green, I., et al., Modern Pathol 8:39 (1995).
Hirt, B., J Mol Biol 26:365 (1967).
Jones, J. L., et al., Science 267:1078–1079 (1995).
Jung, J. U., et al., Mol Cell Biol 14:7235 (1994).
Knowles, D. M., et al., Blood 73:792 (1989).
Korsmeyer, S. J., et al., Proc Natl Acad Sci USA 78:7096 (1981).
Liebowitz, D. and Kieff, E., in Roizman, B., et al. (eds), *The Human Herpesviruses,* Raven Press, New York, N.Y. (1993) p. 107.
Lin, J. C., et al., Blood 81:3372 (1993).
Madeley, C. R. and Field, A. M., *Virus Morphology,* Churchill-Livingstone, London, UK (1988) p. 50–69.
Mathew, S., et al., Genomics 14:775 (1992).
Mesri, E. A., et al., Circ Res 76:161 (1995).
Miller, S. A., et al., Nucleic Acids Res 16:1215 (1988).
Moore, P. S. and Chang, Y., N Engl J Med 332:1181–1185 (1995).
Moore, P. S., et al., J Virol 70:549–558 (1996).
Morfeldt, L. and Torssander, J., Scand J Infect Dis 26:749–753 (1994).
Nador, R. G., et al., N Engl J Med 333:943 (1995).
Pater, M. M., et al., Virology 75:481 (1976).
Pelicci, P. G., et al., J Exp Med 162:1015 (1985).
Raab-Traub, N. and Flynn, K., Cell 47:883 (1986).
Rapp, F., et al., Intervirology 8:272 (1977).
Roizman, B., in Fields, B. N. (ed), *Virology,* Raven Press, New York, N.Y. (1990) p. 1787.
Rosenthal, L. J., et al., Intervirology 19:113 (1983).
Soulier, J., et al., Blood 86:1276–1280 (1995).
Southern, E. M., J Mol Biol 98:503 (1975).
Subar, M., et al., Blood 72:667 (1988).
Thorley-Lawson, D. A., et al., J Immunol 134:3007 (1985).
Walts, A. E., et al., Am J Clin Pathol 94:170 (1990).
Whitby, D., et al., Lancet 346:799–802 (1995).

What is claimed is:

1. A cell line comprising Kaposi's sarcoma-associated herpesvirus, wherein the cell line is designated BC-2 and is deposited with the ATCC as Accession No. CRL 2231.

2. A cell line comprising Kaposi's sarcoma-associated herpesvirus, wherein an Epstein-Barr virus is not present in the cell line and wherein the cell line is designated BC-3 and is deposited with the ATCC as Accession No. CRL 2277.

3. A method of propagating Kaposi's sarcoma-associated herpesvirus, said method comprising:

culturing the cell line of claim 1 under conditions effective to propagate said Kaposi's sarcoma-associated herpesvirus within said cell line.

4. A method of propagating Kaposi's sarcoma-associated herpesvirus in the absence of Epstein-Barr virus, said method comprising:

culturing the cell line of claim 2 under conditions effective to propagate said Kaposi's sarcoma-associated herpesvirus within said cell line.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

AGGAGCGAGA GAGACGGGAT            20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CCAGGTGCCT GCCCACTTCC                                            20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCTAGCTCTT GCAGCAGAAC                                            20

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGGGGTGCCT TACACGTGG                                              19

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CAGTCTGCAG TCATGTTTCC                                            20

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TGTGTGCGTC AGTCTAGTGA G                                          21

(2) INFORMATION FOR SEQ ID NO:7:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCAGTCTCCA GAGTCTTCTC                                                        20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

CGGAGCTAAA GAGTCTGGTG                                                        20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

TGGAGGTGTA GTCTGCTGCG                                                        20

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

CACCCTGAAA CTCCAGGC                                                          18

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GATCCGATCC TCACATAGCG                                                        20

(2) INFORMATION FOR SEQ ID NO:12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

-continued (xi) SEQUENCE DESCRIPTION: SEQ ID NO:12:

CGCCACTCTA TATGCAAACT G                                                                      21

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGATGTCCAC GTCACACTTC                                                                         20